United States Patent [19]

Kataoka et al.

[11] 4,447,207

[45] May 8, 1984

[54] MANDIBULAR MOTION DIAGNOSTIC DEVICE

[75] Inventors: Kenzo Kataoka; Shinichi Nishimoto, both of Otsu; Kazunari Matoba, Nara, all of Japan

[73] Assignee: Kabushiki Kaisha Morita Seisakusho, Kyoto, Japan

[21] Appl. No.: 482,636

[22] Filed: Apr. 6, 1983

[30] Foreign Application Priority Data

Apr. 7, 1982 [JP] Japan .................................. 57-57721

[51] Int. Cl.³ .............................................. A61C 19/04
[52] U.S. Cl. ....................................... 433/69; 128/777
[58] Field of Search ............................. 433/69, 27, 55; 128/777

[56] References Cited

U.S. PATENT DOCUMENTS

| | | | |
|---|---|---|---|
| 2,418,648 | 4/1947 | Kile ....................................... | 433/69 |
| 3,390,459 | 7/1968 | Seidenberg ........................... | 433/27 |
| 4,330,276 | 5/1982 | Becker et al. ........................ | 433/55 |
| 4,386,405 | 5/1983 | Lewin et al. ......................... | 433/69 |

*Primary Examiner*—John J. Wilson
*Attorney, Agent, or Firm*—Koda and Androlia

[57] ABSTRACT

A dental diagnostic device is disclosed, wherein the mandibular motion is created as that which results from synthesis of three-dimensional motions of three points to be measured. It is converted into movement of three reference points for reproduction corresponding to the individual points to be measured and the motion resulting from synthesis of the three-dimensional motions at the respective reference points for reproduction is reproduced in or by the use of the mandibular model. Hence no approximate computing processing or the like is needed, there is no room for errors except those in the measuring and reproducing systems and theoretically it is possible to reproduce with a high precision the patient's mandibular motion by the use of a three-dimensional model of the mandible.

3 Claims, 6 Drawing Figures

MANDIBULAR MOTION DIAGNOSTIC DEVICE

BACKGROUND OF THE INVENTION

1. Field of the Invention

The present invention relates to a mandibular motion diagnostic device for measuring the mandibular motion and reproducing it precisely as motion of a model of the mandible.

2. Prior Art

Analysis of the mandibular motion is an important factor which constitutes the basis for reconstruction of occlusion, diagnosis of gnatho-oral cavity system etc., but hitherto there has been developed no device for precise measurement of the mandibular motion and for reproducing it for close analysis.

Hence, in the occlusal diagnosis, manufacture of crown bridges or prostheses in the dental practice, one has had to resort to adjustments on trial-and-error basis or by methods not only troublesome but also requiring skill. In the manufacture of prostheses, in particular, imperfect adjustment is known to possibly cause gnatho-articular diseases, to say nothing of interfering with satisfactory masticatory function of teeth. The adaptability of prostheses made by such conventional methods to the patient cannot be seen unless they are tested by actually fitting in the mouth of the patient; and the major cause for the inevitable dependence on trial-and-error adjustments has been the absence of effective means for tracing the cause or causes of irregular loads on the condyle head which is known to be most closely associated with gnatho-articular disorders. Hence, it has been and is desireable to have an effective and reliable means, which enable quantitative reproduction of the mandibular motion of individual patients and allow arbitrary setting of the position of condyle head for accurately grasping the motion of condyle head so as to enable proper, reliable diagnosis of irregular motions.

From this point of view, there have been made attempts to measure the mandibular motion by fixing a tiny magnet or spotlight source at the tip of the mandible and detecting the motion of the magnet or light source (e.g. Japanese Patent Publication Sho-52-317, Japanese Patent Publication Sho-57-4253).

All these prior arts, however, grasp the mandibular motion of a single point, and do not measure the motion of the mandible as a whole which is complicated three-dimensional motion. If measurement could be done with a high precision, the motion of the mandible cannot be grasped accurately and analysis made on the basis of such measured data is nothing more than an approximate one. When analysis and diagnosis are made of the mandibular motion reproduced on the basis of such information, accurate and necessary information is difficult to read from general observation of the mandibular motion since it is a three-dimensional motion viewed on a monitor, which is two-dimensional. Since all such efforts amounted to nothing more than a mere simulation, there is a high hurdle to be cleared before proceeding to the next step of reconstruction of the occlusion. Also, despite the fact that proper occlusion, especially in the vicinity of where cusps are engaged, is essential for proper motion of the jaws as a whole, accurate measurement thereof could not be hoped for.

SUMMARY OF THE INVENTION

The object of the present invention is, therefore, to provide a simple, yet precise and practical, diagnostic device for mandibular motion which is effective and useful for the analysis of mandibular motion and dental restorative treatment, especially the manufacture of a prostheses. Such a device comprises a mandibular motion measuring unit consisting of three points to be measured with their relative positions constant with respect to the patient's mandible throughout the time of measurement and three position detectors each thereof provided for each one of the above-mentioned points to be measured so that the movement of each point to be measured is detected as position information as a function of time, a mandibular motion reproducing unit consisting of three reference points for reproducing their relative positions with respect to the mandibular model equal to the relative position of each point to be measured with respect to the above-mentioned patient's mandible and three reference coordinates for reproducing their relative positions with respect to the maxillary model equal to the relative position of individual position detectors with respect to the above-mentioned patient's maxilla so that the position of each reference point reproduced is controlled with respect to the respective reference coordinates for reproduction according to the above-mentioned position information as a function of time for the mandibular model to make relative movement with respect to the maxillary model to have the motion of the patient's mandible precisely reproduced by the mandibular model.

That is, in the present invention, the mandibular motion is grasped as that which results from synthesis of the three dimensional motion of the three points to be measured. The mandibular motion is converted into movement of three reference points for reproduction corresponding to the individual points to be measured and the motion resulting from synthesis of the three dimensional motion at the respective reference points is reproduced in or by the use of the mandibular model; hence no approximate computing processing or the like is needed, there is no room for error except those in the measurement and reproducing system and theoretically it is possible to reproduce with a high precision the patient's mandibular motion by the use of a three-dimensional model of the mandible.

The positions of the points to be measured can be measured as three-dimensional position information. Since, however, the mandibular motion can be grasped as motion of a rigid plane, and the position of a rigid plane in a three-dimensional space and its inclination is bound to be determined by two-dimensional position information of three points set on the rigid plane, its measurement and reproduction are made by the use of two-dimensional information in the following embodiment.

BRIEF DESCRIPTION OF THE DRAWINGS

This and other objects and advantages and further description will now be discussed in connection with the drawings in which.

DETAILED DESCRIPTION OF THE PREFERRED EMBODIMENTS

Figure 1:
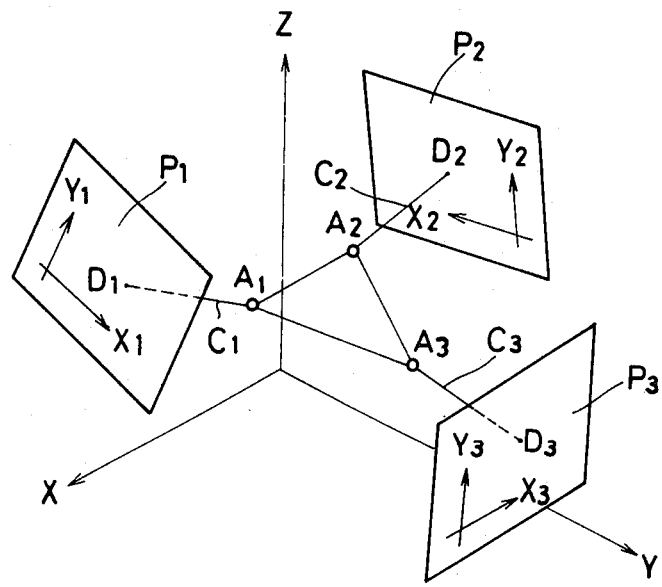
FIGS. 1 and 2 are illustrative views showing the principle of the present invention.
Figure 2:
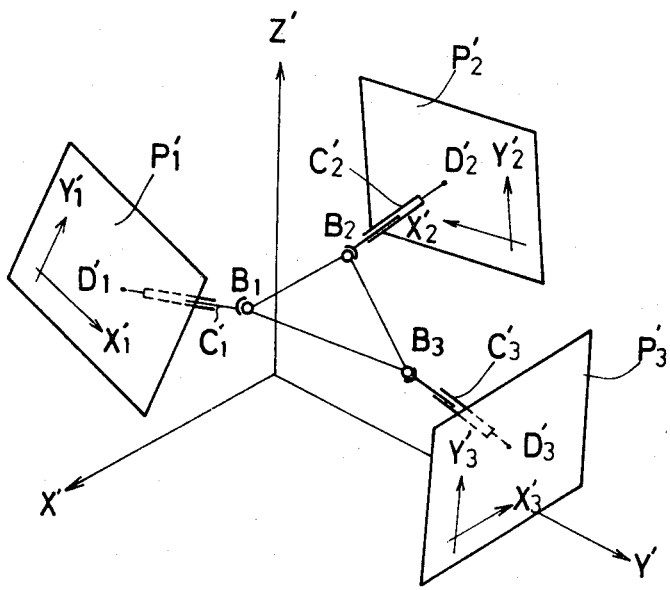

Referring now to FIGS. 1 and 2, the principle of the corresponding relationship between a measuring system and a reproducing system of an embodiment of the present invention is described.

FIG. 1 shows the measuring system in a three-dimensional space represented by coordinates $(X, Y, Z)$, in which $A_1$, $A_2$, $A_3$ are the three points determining a plane corresponding to the mandible and in practical application of the embodiment these are the points to be measured on a rigid body fixed to the mandible. The relative positional relationship among these three points is always constant. $P_1$, $P_2$, $P_3$ are imaginary planes corresponding to $A_1$, $A_2$, $A_3$, and $C_1$, $C_2$, $C_3$, are lines of orthogonal projection from $A_1$, $A_2$, $A_3$ to the imaginary planes $P_1$, $P_2$, $P_3$, and $D_1$, $D_2$, $D_3$ are the corresponding points of orthogonal projection respectively. The measuring systme is capable of measuring on this plane the positional changes of the points of orthogonal projection $D_1$, $D_2$, $D_3$, of $A_1$, $A_2$, $A_3$ onto the planes $P_1$, $P_2$, $P_3$ as separate points of two-dimensional motion coordinates represented by $(X_1, Y_1)$, $(X_2, Y_2)$, $(X_3, Y_3)$ for the respective planes. If the relative positional relationship between $P_1$, $P_2$, $P_3$ is kept unchanged throughout the time of measurement and their positions in the three-dimensional orthogonal coordinate system (Note: These actually are relative inclinations rather than positions. Hence, it is all right if the planes are displaced parallel with their inclinations constant.) are determined. The positions of $A_1$, $A_2$, $A_3$ can be represented by $(X_1, Y_1)$, $(X_2, Y_2)$, $(X_3, Y_3)$. The position of the plane determined by $A_1$, $A_2$, $A_3$ in the three-dimensional space is bound to be established, hence it need not be three-dimensional coordinates such as $(X_1, Y_1, Z_1)$ $(X_2, Y_2, Z_2)$ $(X_3, Y_3, Z_3)$ and can be represented or determined by simpler two-dimensional positional information such as $(X_1, Y_1)$, $(X_2, Y_2)$, $(X_3, Y_3)$. Since the mandibular motion is a three-dimensional motion of plane corresponding to the mandible in a space in which the maxilla is the reference position, it suffices if the coordinates in an arbitrary plane corresponding to the three points to be measured are fixed to the mandible respectively. As mentioned above, however, a prerequisite is that these three arbitrary planes are at positions fixed with respect to the maxilla and the relative positional relationship (inclination of each plane, in particular) is kept unchanged.

FIG. 2 shows a reproducing system in a three-dimensional space represented by the coordinates $(X', Y', Z')$. $B_1$, $B_2$, $B_3$ are three points determining the plane corresponding to the mandible; and in practical application of the embodiment, these are rotatory and freely bendable joints for connection of the mandibular model with the reproducing mechanism, being reference points for reproduction corresponding to $A_1$, $A_2$, $A_3$ in FIG. 1. Also, the triangle $\Delta B_1$, $B_2$, $B_3$ defined by $B_1$, $B_2$, $B_3$ is made to be congruent with the triangle $\Delta A_1$, $A_2$, $A_3$ defined by $A_1$, $A_2$, $A_3$ in FIG. 1. $P'_1$, $P'_2$, $P'_3$ are imaginary planes corresponding to the planes $P_1$, $P_2$, $P_3$ in FIG. 1 and serve as reference coordinate planes for reproduction and are set to have a perfectly identical positional relationship (inclination in particular) with the relative positional relationship among the three planes $P_1$, $P_2$, $P_3$ in FIG. 1. It is so arranged that the members $C'_1$, $C'_2$, $C'_3$ corresponding to $C_1$, $C_2$, $C_3$, as lines of orthogonal projection of $B_1$, $B_2$, $B_3$ to the planes $P_1$, $P_2$, $P_3$, are movable on the respective planes as are points $D'_1$, $D'_2$, $D'_3$ according to the separate pieces of two-dimensional motion coordinate information represented by $(X'_1, Y'_1)$, $(X'_2, Y'_2)$, $(X'_3, Y'_3)$. The members $C'_1$, $C'_2$, $C'_3$ are made to be freely extendible and retractable in directions perpendicular to the respective imaginary planes $P'_1$, $P'_2$, $P'_3$, and are connected with the joints $B_1$, $B_2$, $B_3$. When it is so arranged, the plane defined by $B_1$, $B_2$, $B_3$, if the component members should have an ideal rigidity, can have its position in the space defined by the imaginary planes $P_1$, $P_2$, $P_3$ determined mechanically by the two-dimensional motion coordinate data $(X'_1, Y'_1)$, $(X'_2, Y'_2)$, $(X'_3, Y'_3)$ according to the same principle as described above for the measuring system. When the data $(X'_1, Y'_1)$, $(X'_2, Y'_2)$, $(X'_3, Y'_3)$ are made identical with the two-dimensional motion coordinate data $(X_1, Y_1)$, $(X_2, Y_2)$, $(X_3, Y_3)$, which vary according to the motion measured by the measuring system shown in FIG. 1 as a function of time, the $D'_1$, $D'_2$, $D'_3$ are caused to move in the imaginary planes $P'_1$, $P'_2$, $P'_3$ respectively, the positions $B_1$, $B_2$, $B_3$ are determined accordingly. Since $B_1$, $B_2$, $B_3$ are freely rotatable and bendable joints, the inclination of the plane defined thereby, too, is determined by the perpendicularity (errors) of $C_1$, $C_2$, $C_3$ to the respective imaginary planes and the pulling urges of the rigid members, the three-dimensional motion of the plane determined by $B_1$, $B_2$, $B_3$ is reproduction of the three-dimensional motion of the plane determined by $A_1$, $A_2$, $A_3$. In practice, since the mandibular motion is with respect to the maxilla as mentioned above, three-dimensional measurement and three-dimensional reproduction of the mandibular motion are feasible if the above arrangement is taken with the relative positions of the imaginary planes $P_1$, $P_2$, $P_3$ with respect to the maxilla in the measuring system made to agree with the relative positions of the imaginary planes $P'_1$, $P'_2$, $P'_3$ with respect to the maxillary model and the position of the mandible and the relative positional relationship among $A_1$, $A_2$, $A_3$ in the measuring system with the mandibular model and the relative positional relationship among $B_1$, $B_2$, $B_3$ respectively.

When this arrangement is taken in the measuring and reproducing systems to determine a complex three-dimensional motion such as the mandibular motion, it can be determined by three pairs of two-dimensional position information, namely $(X_0, Y_0)$, $(X_1, Y_2)$, $(X_2, Y_3)$, and three-dimensional information such as $(X_0, Y_0, Z_0)$ is not needed. Hence, the measuring factors can be greatly simplified and two-dimensional position factors suffice also for reproduction. However, the occlusal motion has involved in it complex motions such as torsional and rotary motion accompanied by shifting of the center of rotation. Hence, it is difficult to make an intricate mechanism similar to the human body to reproduce this motion and at the same time a very complicated computation is required for reproducing such a motion in or by means of a mechanical equivalent to the human body from the data expressed by such three-dimensional coordinates. When it is reduced to two-dimensional position information as in this embodiment, however, it suffices to make a simple reproducing mechanism with a two-dimensional position control function which is capable of moving according to two-dimensional position information. Hence, complicated computation is not needed; and also, since measurement of two-dimensional positions suffices in the measuring system, the required measurement is extremely easy yet very high in precision compared with the three-dimensional counterpart, and it is feasible to do even with simple length-measuring sensors. Moreover, in this embodiment, the relative positional relationship between the points to be measured $A_1$, $A_2$, $A_3$ in the measuring system is made to match that between the joints $B_1$, $B_2$, $B_3$ which is determined by the movement of $D'_1$, $D'_2$, $D'_3$ on each plane of the reproducing system in order to further facilitate the data-processing between the measuring system and the reproducing system. Hence, reproduction of a three-dimensional motion in the reproducing system on the basis of two dimensional position information from the measuring system is feasible without the necessity of computation; whereas, highly complicated computation is essential if reproduction of such a motion should be made with these positional relationships not matching.

Figure 3:
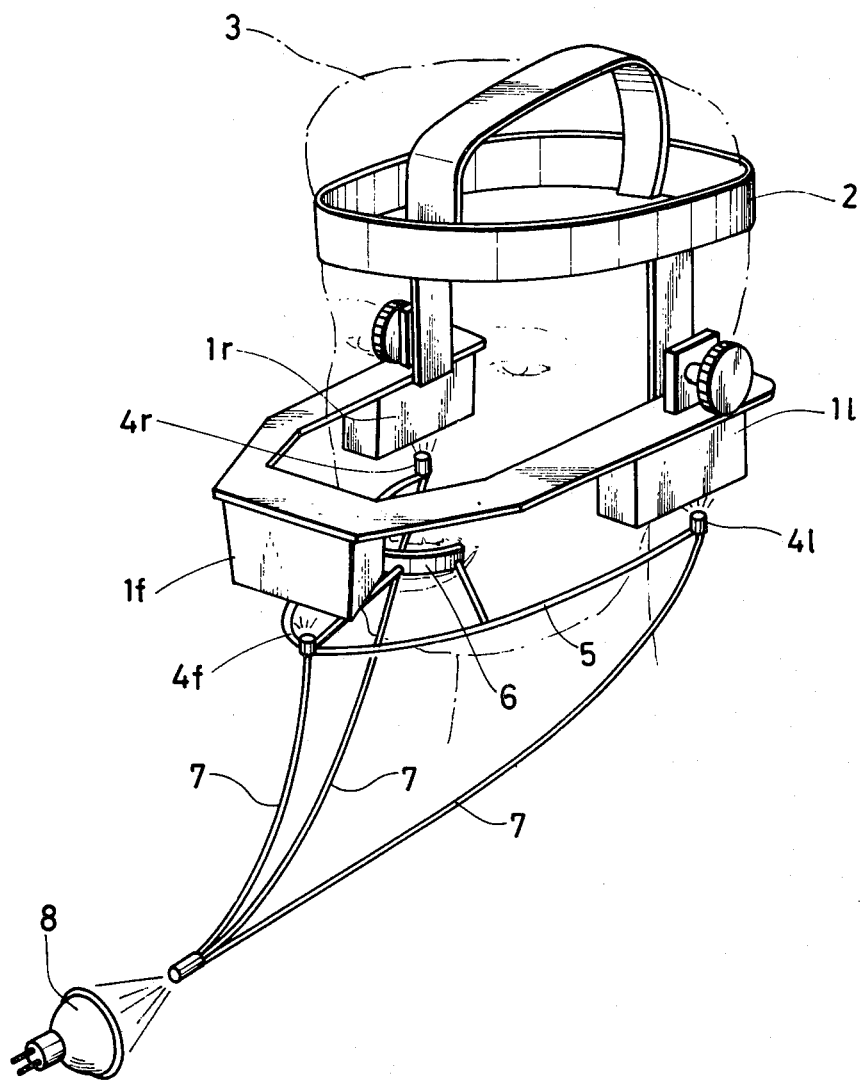
FIG. 3 is a schematic perspective view of the mandibular motion measuring unit in one embodiment of the present invention.

Now described is the mandibular motion measuring unit corresponding to the measuring system in FIG. 1. In FIG. 3 $1r$, $1l$, $1f$ are position detectors having built in them photoelectric conversion elements, 2 is a head band which is to be fixedly attached to the head (that is, maxilla) of the patient 3 in order to hold the position detectors $1r$, $1l$, $1f$ in a predetermined relative positional relationship, $4r$, $4l$, $4f$ are spotlight sources $4r$, $4l$, $4f$ in a predetermined positional relationship, 6 is a clutch used to fix the looped bar to the mandible of the patient 3, 7 are photo-fibers for supplying light to the spotlight sources $4r$, $4l$, $4f$ and 8 is a main light source.

The spotlight sources $4r$, $4l$, $4f$ correspond to the points to be measured $A_1$, $A_2$, $A_3$ and determine a plane representing the mandible. The two-dimensional position information for the spotlight sources $4r$, $4l$, $4f$ reflecting the imaginary planes $P_1$, $P_2$, $P_3$ in FIG. 1 are detected by the position detectors $1r$, $1l$, $1f$ for the individual spotlight sources. Since, as seen from the figure, each position detector has its position fixed with respect to the maxilla, it can be located arbitrarily without interfering with the conditions for the imaginary planes $P_1$, $P_2$, $P_3$. Changes in the positions of the spotlight sources $4r$, $4l$, $4f$ accompanying the occlusal motion can thus be detected on the three imaginary planes to be outputted to the computing unit.

Figure 4:
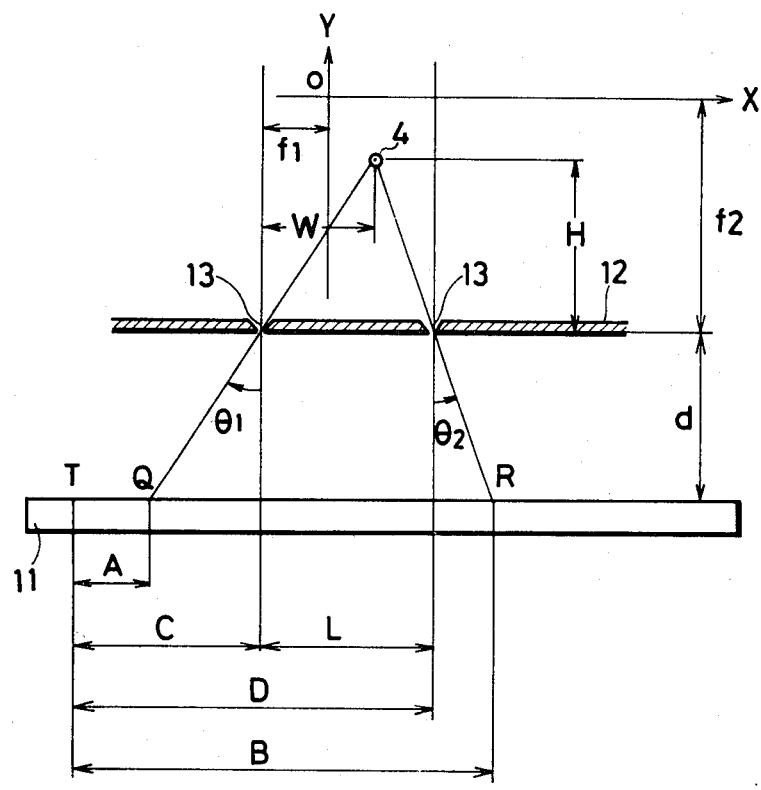
FIG. 4 is an illustrative view showing the principle of a position detector of the mandibular motion measuring unit thereof.

FIG. 4 is a sketch showing the working principle and construction of the position detectors $1r$, $1l$, $1f$. In the Figure, 11 is a linear photoelectric conversion element (hereinafter simply referred to as "element") such as a CCD linear image sensor, 12 is a screening plate disposed in front of and parallel to the element 11 and has in it two slits 13 in perpendicular relationship with the longitudinal direction of the element 11, and 4 is a light source. When the point of origin is determined as illustrated with the axis parallel to the longitudinal direction as the X-axis and the axis perpendicular to the element 11 and screening plate 12 as the Y-axis, the position of the spot light source 4 on the (x, y) coordinate system can be obtained as follows. That is, when the individual dimensions and angles are determined as illustrated with the point of origin on the element 11 as T, and the positions at which the ray having passed the slit 13 hits the element as Q and R, there is obtained the following simultaneous equations:

$$\tan \theta_1 = \frac{W}{H} \quad (1)$$

$$\tan \theta_2 = \frac{L - W}{H} \quad (2)$$

When these simultaneous equations are solved to determine the values H and W:

$$H = \frac{L}{\tan \theta_1 + \tan \theta_2}$$

$$W = \frac{L \tan \theta_1}{\tan \theta_1 + \tan \theta_2}$$

and when coordinates (x, y) of the spot light source 4 are expressed by the equations (3) and (4) below:

$$x = W - f_1 = \frac{L \tan \theta_1}{\tan \theta_1 + \tan \theta_2} - f_1 \quad (3)$$

$$y = H - f_2 = \frac{L}{\tan \theta_1 + \tan \theta_2} - f_2 \quad (4)$$

$$\text{where: } \tan \theta_1 = \frac{C - A}{d}$$

$$\tan \theta_2 = \frac{B - D}{d}$$

Since $f_1$, $f_2$, L, d, C, D are already known, the position of the spot light source 4 on the (x, y) coordinate system can be obtained by detecting the positions Q and R on the element 11 electrically and obtaining A and B from their differences from T. Even if the spot light source 4 should be displaced in the direction perpendicular to the (x, y) coordinate plane, Q and R in FIG. 4 remain unchanged for they are displaced only parallel with the slits 13, hence the result of measurement is not affected.

As seen from FIG. 3, the right and left position detectors $1r$, $1l$ are disposed parallel to each other with their longitudinal axes along the level, longitudinal (front-rear) axis of the head, while the front position detector $1f$ is disposed with its longitudinal direction sideways and perpendicular to the longitudinal axes of the position detectors $1r$, $1l$. Since the incident rays from the spot light sources $4r$, $4l$, $4f$ are all from under the respective position detectors, the position detectors $1r$, $1l$ detect information of the positions on two imaginary planes with their longitudinal and vertical axes agreeing with the x and y axes in FIG. 3, respectively; while the position detector $1f$ detects information of the positions on an imaginary plane with its lateral and vertical axes agreeing with the x and y axes in FIG. 3, respectively.

Figure 6:
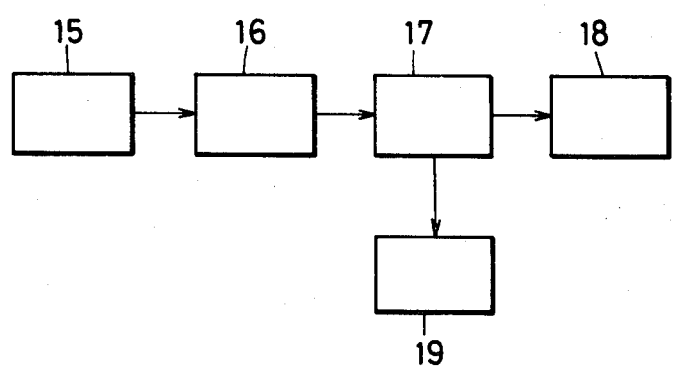
FIG. 6 is a block diagram showing a position information processing circuitry thereof.

The three-dimensional position information of the mandible reduced to three pairs of two-dimensional elements is measured successively a predetermined number of times (e.g. 3,000 times) at intervals of a minute length of time (e.g. 1 ms–2 ms) in order to determine the mandibular motion, and the result is recorded as position information as a function of time. FIG. 6 is a block diagram of the position information processing circuit. Each piece of position information detected by the measuring unit 15 is sent to the computing unit 16, and is converted into a corresponding piece of data in a form suitable for diagnosis or for reproduction before it is stored in the memory unit 17. When the computation is completed, the stored data is outputted to the reproducing unit 18. The memory unit 17 is also capable of displaying the information of movement of each point measured on a cathode ray tube (CRT) 19.

Figure 5:
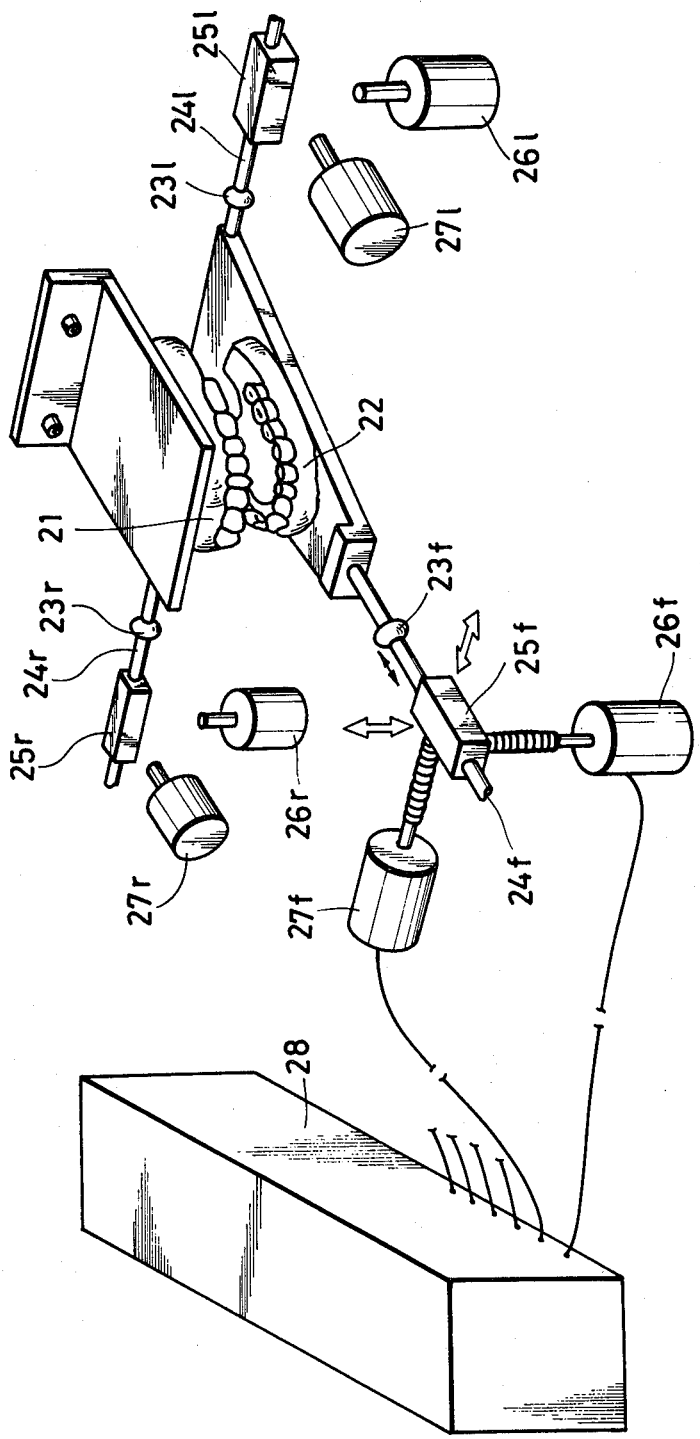
FIG. 5 is a schematic perspective view of the mandibular motion reproducing unit thereof.

FIG. 5 shows a mandibular motion reproducing unit corresponding to the reproducing system in FIG. 2 and the reproducing system 19 in FIG. 6. In FIG. 5, 21 is a mandibular model, 22 a maxillary model, 23r, 23l, 23f are freely rotatable and bendable joints connected with the mandibular model in a predetermined positional relationship, 24r, 24l, 24f are movable members with their leading ends connected with the joints 23r, 23l, 23f respectively and held by holders 25r, 25l, 25f to be freely slidable, 26r/27r, 26l/27l, 26f/27f are pulse motors for driving the holders 25r, 25l, 25f, and 28 is a motor controller. The joints 23r, 23l, 23f correspond to the reference points for reproduction $B_1$, $B_2$, $B_3$ in FIG. 2, and the positional relationship between the individual joints is arranged to be identical with that between the three spot light sources 4r, 4l, 4f, that is, the three points to be measured. The holders 25r, 25l, 25f are supported to be movable in the reference coordinate plane corresponding to the planes $P'_1$, $P'_2$, $P'_3$, that is, the three imaginary planes defined by the position detectors 1r, 1l, 1f, and it is so arranged that the three movable members 24r, 24l, 24f are invariably perpendicular to the respective imaginary planes regardless of their positions in the reference coordinate plane. These holders 25r, 25l, 25f are shifted by the pulse motors 26r/27r, 26l/27l, 26f/27f so that the movement of the center axes of the movable members 24r, 24l, 24f is controlled by the two-dimensional coordinates of the positions with respect to the respective planes outputted from the memory unit 17. The plane representing the mandible and defined by the three joints 23r, 23l, 23f is caused to move and the mandibular model 22 exactly follows the mandibular motion of the patient for reproduction thereof.

In this embodiment, as mentioned above, the mandibular motion measuring unit and the mandibular motion reproducing unit are arranged to have their positional relationship substantially identical to that between the measuring system and the reproducing system in FIGS. 1 and 2 respectively. The mandibular motion, which is three-dimensional, is detected and reduced to secondary position information as a function of time; and the three-dimensional mandibular motion is reproduced by simultaneously controlling the positions of the three points defining the plane representing the mandible. The velocity of the motion as it is reproduced can be controlled arbitrarily as necessary, and it is of course possible to stop it half-way. In the above explanation it is assumed that the triangles defined by the three points to be measured in the measuring system and the three reference points for reproduction in the reproducing system are congruent with each other; but these can be similar to each other, and, in this case, the extent of movement of each reference position for reproduction is varied according to the dimensional ratio therebetween. This can be easily done in the computing unit 16, and it is even possible to use an enlarged model for still closer analysis.

As is apparent from the above description of the embodiment, the present invention relates to a mandibular motion diagnostic device wherein the mandibular motion is detected as position information as function of time by three position detectors each provided for each point to be measured through measurement of the movement thereof. After the necessary computational processing, a motion substantially identical with the patent's mandibular motion is reproduced by the use of a mandibular model through control of the reproducing mechanism according to the processed data. Hence it enables accurate reproduction of motion of the mandible, which is a complex three-dimensional motion having involved therein (1) simple rotary motion, (2) rotary motion accompanied by shifting of the center axis thereof, (3) torsional motion, (4) combination of (2) and (3) forms of motion and so on for proper analyses and diagnoses Thus, a device which is extremely effective and useful for diagnosis as well as treatment, manufacture of prostheses in particular, with its features of facilitating repeated observation of isolated phenomena as well as low-speed observation of high-speed phenomena, with the possibility of storing the measured data and dispensing with the necessity of the dentist attending to the patient each time, and enabling comparison of the conditions before and after treatment and so forth is provided.

We claim:

1. A mandibular motion diagnostic device comprising:
   a mandibular motion measuring unit including:
      a head band for a patient;
      at least three position detectors coupled to said head band, each of said position detectors being provided at predetermined points to be measured and having a fixed position relative to a mandible of said patient, each of said position detectors comprising:
         a linear photo-electric conversion element;
         a screening plate disposed in front of said linear photo-electric conversion element; and
         at least two slits provided in said screening plate; and
      a clutch for being coupled to said mandible of said patient;
      a loop bar coupled to said clutch and extending around said mandible;
      at least three light sources provided on said loop bar in a single plane and adjacent said position detectors, said three light sources comprising:
         at least three photo-fibers, one each extending to a point adjacent said position detectors; and
         a single source of light for supplying light to said photo-fibers; and
      whereby the movement of said each point to be measured is detected as position information as a function of time; and
   a mandibular motion reproducing unit including:
      three reference points for reproducing their relative positions with respect to a mandibular model equal to said relative positions of each point to be measured with respect to said patient's mandible; and
      three reference coordinates for reproducing their relative positions with respect to maxillary model equal to said relative positions of individual position detectors with respect to said patient's maxilla so that said position of each reference point for reproduction is controlled with respect to said respective reference coordinates for reproduction according to said position information as a function of time for said mandibular model to cause relative movement with respect to said maxillary model to reproduce said patient's mandible movement precisely with said mandibular model.

2. A mandibular motion diagnostic device as defined in claim 1, wherein said position information for said three points to be measured is obtained as two-dimensional coordinate data through orthogonal projection of said three points to be measured onto respective two-dimensional coordinate planes of said position detectors, and said three reference points for reproduction have their positions controlled according to said two-dimensional coordinate data on said reference coordinate planes for reproduction in a mutual positional relationship equal to that between said two-dimensional coordinate planes of said position detectors.

3. A mandibular motion diagnostic device as defined in claim 2, wherein three movable members freely movable in a direction perpendicular to each reference coordinate plane for reproduction and having their positions with respect to said reference coordinate planes for reproduction controlled according to said two-dimensional coordinate data are connected with said mandibular model through freely rotatable and bendable joints and are set to have their centers of rotation as well as bending agreeing with the corresponding reference points for reproduction.

* * * * *